United States Patent
Guarascio et al.

(10) Patent No.: US 11,213,457 B2
(45) Date of Patent: Jan. 4, 2022

(54) PORTABLE SECURE PILL DISPENSER WITH FAILSAFE

(71) Applicants: Anthony John Guarascio, Naples, FL (US); Richard Michael Ribellino, Jr., Naples, FL (US)

(72) Inventors: Anthony John Guarascio, Naples, FL (US); Richard Michael Ribellino, Jr., Naples, FL (US)

(*) Notice: Subject to any disclaimer, the term of this patent is extended or adjusted under 35 U.S.C. 154(b) by 0 days.

(21) Appl. No.: 16/865,947

(22) Filed: May 4, 2020

(65) Prior Publication Data
US 2021/0244619 A1    Aug. 12, 2021

Related U.S. Application Data

(60) Provisional application No. 62/972,990, filed on Feb. 11, 2020, provisional application No. 63/003,327, filed on Apr. 1, 2020.

(51) Int. Cl.
*A61J 7/00*    (2006.01)
*A61J 1/03*    (2006.01)
*A61J 7/02*    (2006.01)

(52) U.S. Cl.
CPC ............ *A61J 7/0076* (2013.01); *A61J 1/03* (2013.01); *A61J 7/02* (2013.01)

(58) Field of Classification Search
CPC .............. A61J 7/0076; A61J 7/02; A61J 1/03
See application file for complete search history.

(56) References Cited

U.S. PATENT DOCUMENTS

| 5,797,515 A * | 8/1998 | Lift ................. G16H 20/13 221/2 |
| 7,048,141 B2 * | 5/2006 | Abdulhay ............ G07F 11/10 221/15 |
| 10,562,696 B2 * | 2/2020 | Yeo .................. B65D 83/0409 |
| 2003/0222090 A1 * | 12/2003 | Abdulhay ............ G07F 11/70 221/3 |
| 2008/0283542 A1 * | 11/2008 | Lanka ................. G07F 17/0092 221/6 |
| 2009/0159608 A1 * | 6/2009 | Shoenfeld ........... G16H 20/13 221/1 |
| 2009/0281657 A1 * | 11/2009 | Gak .................. G16H 20/13 700/242 |

(Continued)

OTHER PUBLICATIONS

Konrad, Walecia, "Mistakes in Storage May Alter Medication", The New York Times, Aug. 15, 2011, https://www.nytimes.com/2011/08/16/health/16consumer.html.

(Continued)

*Primary Examiner* — Michael Collins
(74) *Attorney, Agent, or Firm* — Woodard, Emhardt, Henry, Reeves & Wagner, LLP

(57) ABSTRACT

A medication dispensing and monitoring system of the present invention includes a housing containing an interior for storing and dispensing medication to an authorized patient at a desired time. The invention is programmed to dispense medication at the desired time and activates alarms if the proper procedure is not completed and/or if other undesirable events occur. The invention includes a secondary dispenser as a failsafe to ensure that the patient can obtain a dose of the contained medication in the event of a device malfunction or patient error.

20 Claims, 8 Drawing Sheets

(56) References Cited

U.S. PATENT DOCUMENTS

| | | | | |
|---|---|---|---|---|
| 2010/0318218 | A1* | 12/2010 | Muncy, Jr | B65D 83/0409 |
| | | | | 700/220 |
| 2013/0116818 | A1* | 5/2013 | Hamilton | A61J 7/04 |
| | | | | 700/236 |
| 2013/0200033 | A1* | 8/2013 | Zonana | B65D 83/0409 |
| | | | | 215/231 |
| 2014/0236349 | A1* | 8/2014 | Bae | B65B 1/46 |
| | | | | 700/236 |
| 2014/0277710 | A1* | 9/2014 | Akdogan | A61J 1/03 |
| | | | | 700/241 |
| 2015/0227127 | A1* | 8/2015 | Miller | G16H 20/13 |
| | | | | 700/244 |

OTHER PUBLICATIONS

University of Maryland. "Scientists develop first fabric to automatically cool or insulate depending on conditions: Researchers have created a fabric that dynamically regulates heat passing through it." ScienceDaily. ScienceDaily, Feb. 7, 2019. <www.sciencedaily.com/releases/2019/02/190207142242.htm>.

\* cited by examiner

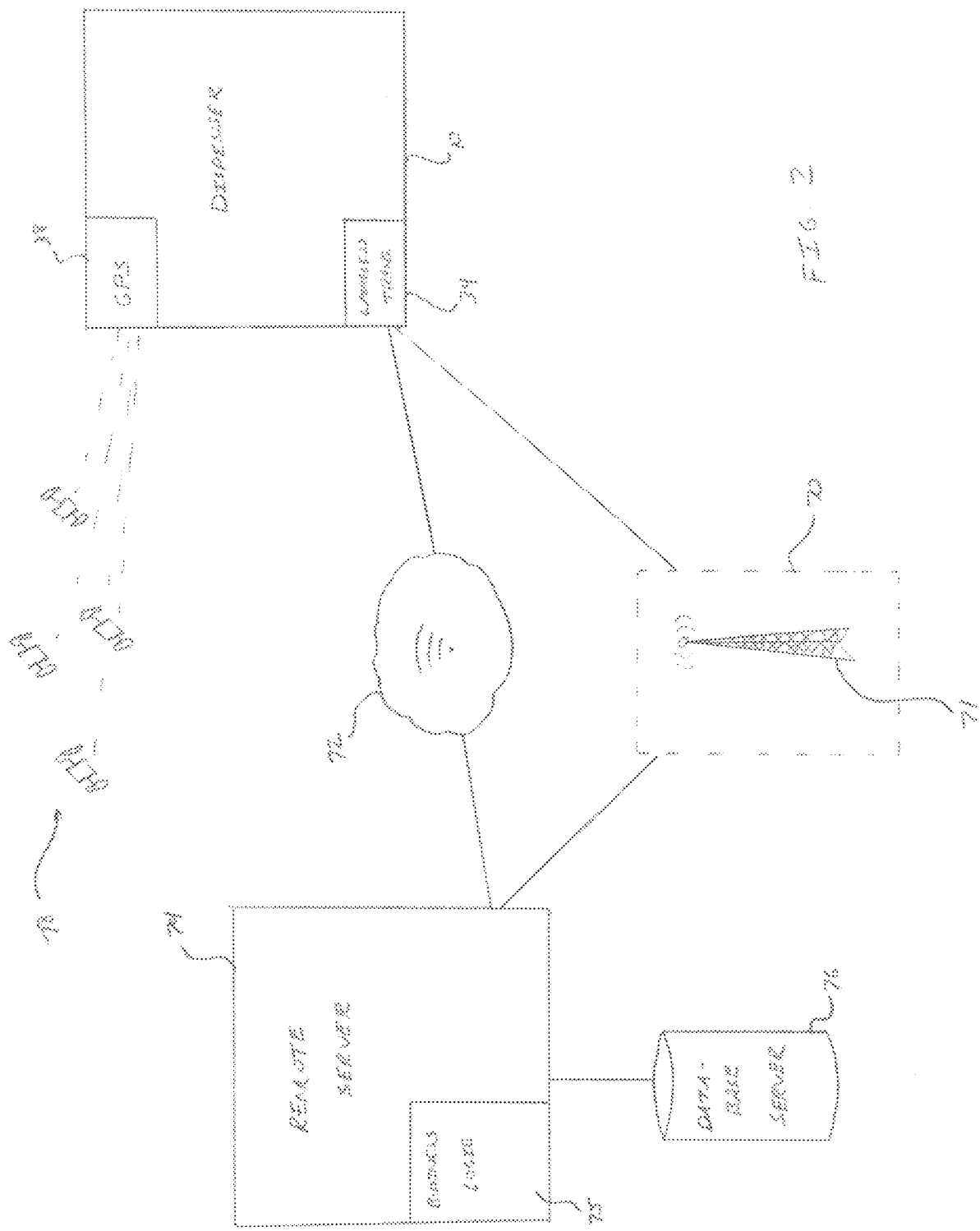

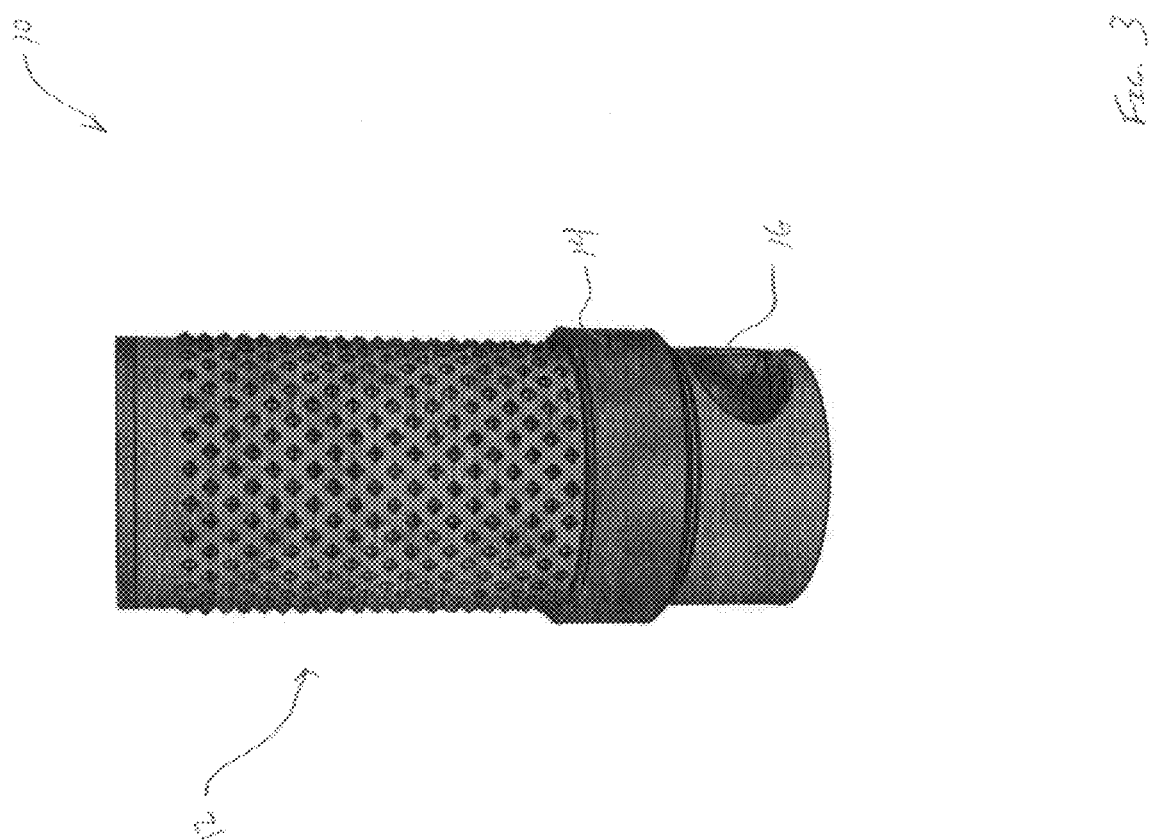

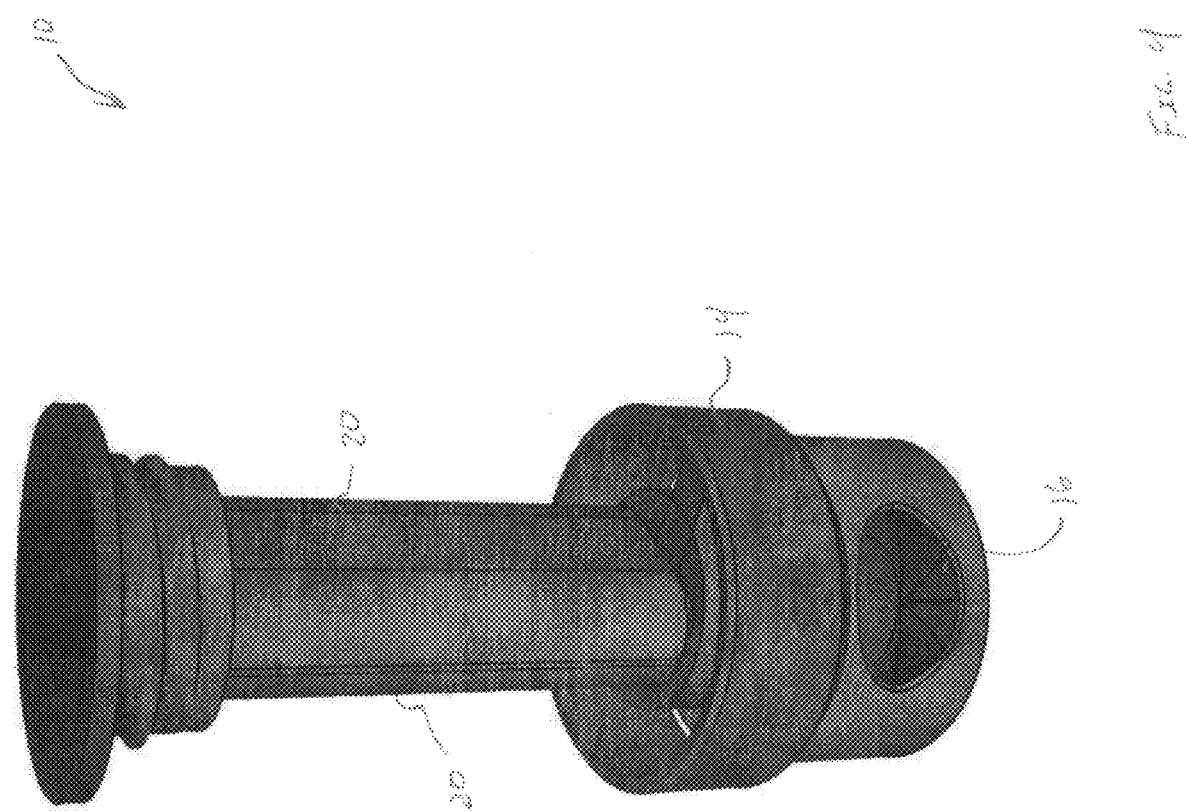

500
START

502
Patient is prescribed a medication

504
Patient selects a pharmacy to fulfill the prescription such as bringing prescription to pharmacy's physical location or by having the prescription electronically submitted 506
It is determined that the prescription should be filled using a portable secure pill dispenser 508
A new, used or sterilized portable secure pill dispenser is selected by pharmacist or other authorized individual filling the prescription 510
The selected portable secure pill dispenser may have a full battery or may require a new or rechargeable battery 512
Pharmacist or other authorized individual fills the portable secure pill dispenser with the correct quantity of the prescribed medication 514
Pharmacist or other authorized individual or software designated by them, must program the portable secure pill dispenser to the patient and prescription 516
Once data is confirmed and verified, the patient is trained on how to use the portable secure pill dispenser 518
Patient is released with portable secure pill dispenser

520
END

Fig. 5

600
START

602
Patient takes possession of the portable secure pill dispenser after having been freshly loaded with patient's prescribed medication 604
The wireless transceiver begins communicating with remote server to initialize 606
Patient requests the dispensation of one or more pills 608
Dispenser attempts to dispense the pill(s) into the pill holding area by activating the first dispenser 610
After each first dispenser, the pill detector determines whether or not a pill was actually dispensed into the pill holding area 612
In the event the pill is not detected 614
The processing unit may attempt to activate first dispenser one or more times until successful 616
If unable to verify the dispensation of a pill using the pill detector, the processing unit may fail over and attempt to dispense pill using second dispenser 618
After activation of second dispenser, pill detector again seeks to verify the proper dispensation and is able to do so 620
The process proceeds to the occurrence of a predetermined event, the attempt by the patient to dispense a second pill immediately following a first dispensation 622
The dispenser and processing unit report this event to remote server using wireless transceiver

Fig. 6

624
Upon receipt, the remote server stores data regarding the event in association with the patient in its database and may also take any actions programmed therein, i.e. notify proper authorities, prescribing physician or attending pharmacist 626
The process concludes with patient completing the course of the medication and returning the dispenser to the appropriate issuing entity

628
END

Fig. 6 Cont'd

700
START

702
Used portable secure pill dispenser received back from patient

704
Patient to which the dispenser was previously assigned is identified and disassociated in the remote server 706
The remaining medicine within the dispenser is logged and stored in association with the patient and prescription within database by remote server 708
Remaining medicine is disposed of in a responsible way approved by the appropriate agencies 710
Dispenser is then put through a sanitization process and then tested to ensure proper operation 712
Dispenser is then recharged or fitted with a replacement battery 714
Dispenser is then repackaged and redeployed to a distributor, pharmacy or other authorized user for redeployment and reuse

716
END

Fig. 7

PORTABLE SECURE PILL DISPENSER WITH FAILSAFE

CROSS-REFERENCE TO RELATED APPLICATIONS

This application claims the benefit of U.S. Provisional Application Ser. No. 62/972,990, filed Feb. 11, 2020 and U.S. Provisional Application Ser. No. 63/003,327, filed Apr. 1, 2020, each of which is hereby incorporated by reference in its entirety.

FIELD OF THE INVENTION

The present invention relates generally to containers and/or dispensers for medication and more particularly pertains to a secured pill container capable of being tracked while also monitoring and safely and reliably controlling dosing.

BACKGROUND OF THE INVENTION

In the United States, over 4.3 billion retail prescriptions are filled annually. Most are distributed in a simple childproof prescription drug container having an entire course or a periodically refillable supply of medication, such as one month's worth. Unfortunately, given the simplicity of immediate access to the entire supply of pills once they leave the pharmacy, many of these prescriptions are abused, meaning that they are utilized other than for their intended purpose. Alternatively, prescription medications are frequently used in a way which fails to comply with the prescribing doctor's intent.

Experts estimate that more than 18 million people ages 12 and older have used prescription drugs for nonmedical reasons in the previous year. That represents more than 6% of the U.S. population. More people report using controlled prescription drugs than cocaine, heroin, and methamphetamine combined. That puts prescription drugs second behind marijuana when it comes to illicit drug use. Most abused prescription drugs fall under four categories, painkillers, tranquilizers, stimulants and sedatives. As such, a need exists to further control the availability and use of prescription medications, particularly those which are commonly abused.

Regarding lack of dosing compliance, a recent survey indicates that 57% of patients forget to take their prescription medication at least once. This number, and the frequency of occurrence of the error, increases dramatically when the daily dosage frequency and/or the age of the patient increases. This can lead to increased relapse, increased hospitalizations and a greater overall cost of care, with a significant adverse impact upon patient's health outcome.

Numerous systems seeking to tackle one or more of these problems exist, including prescription drug locks for containers, regimented pill dispensers and the like. However, despite these types of devices, many drawbacks exists which prevent them from becoming a widely utilized solution. Typically the prescription drugs which are the most important to control are also the most critical for the patients. As such, a locking prescription drug container creates many potential issues, especially for these critical medications, in the event of a malfunction, lost device, or inability of the patient to properly operate the device Moreover, all 50 states have prescription drug monitoring programs (PDMPs) that actively track in-state prescriptions, but without any ability to track and/or control actual usage of the prescription medication in the patient's hands, these systems are woefully inadequate.

BRIEF DESCRIPTION OF THE DRAWINGS

FIG. 2 is a plan view of a representative deployment of the portable secure pill dispenser of FIG. 1 in use with existing and additional infrastructure according to one form of the present invention.

FIG. 3 is a perspective design view of the exterior housing of another embodiment of a portable secure pill dispenser.

FIG. 4 is another perspective design view of the portable secure pill dispenser of the form shown in FIG. 3, but having the upper portion of exterior housing and related components secured thereto hidden from view.

FIG. 5 is a flowchart illustrating one set of steps involved in the configuration and deployment of a portable secure pill dispenser, such as that shown in FIG. 1.

FIG. 6 is a flowchart illustrating one set of steps involved in the exemplary operation of the portable secure pill dispenser shown in FIG. 1.

FIG. 7 is a flowchart illustrating one set of steps involved in the process of receiving a return of a portable secure pill dispenser and reconditioning it for subsequent use.

SUMMARY

Figure 1:
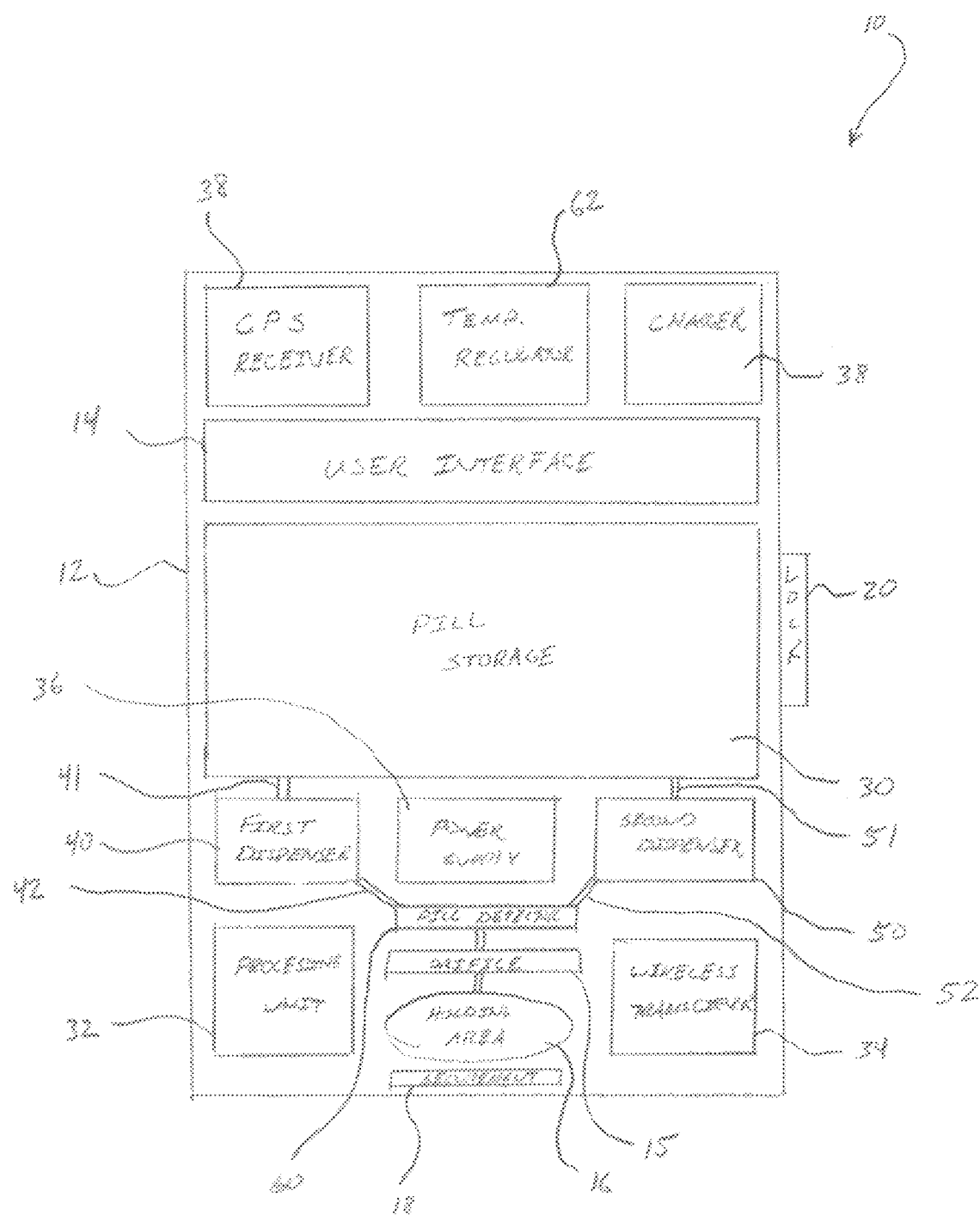
FIG. 1 is a plan view of a portable secure pill dispenser according to one embodiment of the present invention.

Disclosed is a secure portable pill dispenser having capability of tracking and aiding in patient compliance with a prescribed dosing regimen. The dispenser is operable to controllably release medication or pills to a patient at only controlled times to prevent abuse. The dispenser is also operable to notify the patient of the need for a dose, so as to increase patient compliance. The dispenser also include redundant dispensers, and potentially at least one redundant dose, in order to ensure availability of medication to the patient in the event of a malfunction or other emergency.

Other objects and attendant advantages will be readily appreciated as the same become better understood by references to the following detailed description when considered in connection with the accompanying drawings.

DESCRIPTION OF THE ILLUSTRATED EMBODIMENTS

For the purposes of promoting an understanding of the principles of the disclosure, reference will now be made to the embodiments illustrated and specific language will be used to describe the same. It will nevertheless be understood that no limitation of the scope of the disclosure is thereby intended, such alterations, modifications, and further applications of the principles being contemplated as would normally occur to one skilled in the art to which the invention relates.

FIG. 1 provides a plan view of a portable secure pill dispenser 10 (also referred to herein as "dispenser 10") according to one embodiment of the present invention. Beginning with the exterior features, the portable secure pill dispenser 10 includes an exterior housing 12 which may be in the shape of a tradition pill bottle or in some other shape, such as a being substantially in the shape of a cylinder, rectangle, circle, oval or the like. However, the shape of the dispenser 10 is not important to the present invention, but could be designed to provide for increased convenience or portability as well as product design aesthetics. The outside surface of the exterior housing 12, or some portion thereof, may be formed from or covered in non-slip or other high-friction material(s) to prevent accidental dropping of the dispenser 10. Alternatively or additionally, the exterior housing 12, or some portion thereof, is formed from a durable and resilient material, such as plastic, polycarbonate, metal or the like. In a further form, a more durable material would be selected to prevent tampering with or improperly gaining access to the pills contained therein.

Portable secure pill dispenser 10 also includes a user interface 14, which is accessible to the patient on the exterior of the dispenser 10. User interface 14 may be a touch screen user interface in which a number of patient selectable options are provided. For example, user interface 14 may include one or more logical buttons which enable selective activation of the dispenser 10 including the request for dispensing a pill, a security authentication or verification and/or programming of the dispenser 10 by an authorized entity for use by the end patient. Additionally, when the user interface 14 is provided in a touch screen, the buttons may be dynamically changed as each menu or function requires. Alternatively or additionally, physical buttons may be provided as part of user interface 14 to enable selective activation of the dispenser 10 including the request for dispensing a pill, a security authentication or verification or other functions. In order to conserve space and thus the overall size of the dispenser 10, a limited number of physical buttons is preferred, such as between two and five buttons, but more or less may be provided.

Secure pill dispenser 10 also has an externally accessible pill holding area 16, which is an at least partially enclosed volume to temporarily holds pills after they are intentionally dispensed by dispenser 10 but before the patient takes the pills. The pill holding area 16 may be defined within exterior housing 12. In one form, the pill holding area 16 is a recess formed within the exterior housing 12. The recess may be square shaped, rectangular, rounded or otherwise and preferably provides sufficient space for at least two pills simultaneously. In one form, the pill holding area 16 includes a securement mechanism 18, such as a vertically sliding door or other cover or seal, which ensures that the dispensed pills remain within the pill holding area 16 until they are collected by the patient, who may be required to enter a combination or otherwise authorize access to the pill holding area 16. This securement mechanism 18 may also be utilized as a second line of defense to prevent the accidental dispensation of pills, such as to an unauthorized person or to a child.

Secure pill dispenser 10 also includes an access control 20 which secures access to the interior of the external housing 12. Access control 20 may be a lock which secures two or more parts of the exterior housing 12 to one another or may secure a lid, cap or bottom onto the exterior housing 12, or may otherwise permit access to the interior of the external housing 12. The access control 20 may be electronically controlled or controlled by a key or other known access control mechanism. In one form, the access control 20 may not be operated by the end patient, but rather is reserved for access by the issuing entity, such as a manufacturer, pharmacy, pharmacist or other entity in the medical field.

Turning to the interior of the portable secure pill dispenser 10, a pill storage 30 is provided which secures the pills to be dispensed. The pill storage area 30 is preferably of sufficient size to store between 10 and 100 pills of common and known size, so as to cover the most common prescription/refill quantities, but larger or smaller sizes are possible and contemplated. The pill storage area 30 may be an open space in which the pills are free to move about or may be more structured, such as a cartridge or other ordered pill track. One example of an ordered pill track is a spring loaded pill track in which each pill is urged toward the end of the track after being loaded therein, much like those commonly used in toy candy dispensers from Pez Candy USA. In the event an open space pill storage area 30 is utilized, baffles may be incorporated the prevent pill breakage or damage, while the smallest dimension of the pill storage area 20 may also be reduced to between the width of a typical pill and less than four times the width of a typical pill, in order to further reduce this likelihood. Moreover, for an open space pill storage area 20, a gravity feed or other design may be utilized to feed pills to a desired area, such as the dispensers described below, to assist with the intended operation. In a further form, an agitator (not shown) or other mechanism to increase the speed and position of the pills to be dispensed as intended may be provided.

Portable secure pill dispenser 10 also includes a processing unit 32 and a wireless transceiver 34, each of which may be powered by a power supply 36. User interface 14 may also be powered by power supply 36, if necessary. In some forms, a charger 38 may also be included to replenish power supply 36. In the illustrated form, the processing unit 32 includes at least one processor, state machine or other mechanical and/or electronic logic for controlling one or more of the components of portable pill dispenser 10. Processing unit 32 may also include transitory and non-transitory memory for data storage (not separately shown). The operation of processing unit 32, as well as its memory usage, will be described further herein, including in FIG. 6. Wireless transceiver 34 is a cellular communication device, such as a cellular radio, operating on a known cellular network, such as the GSM, LTE or CDMA wireless networks operated by AT&T or Verizon Wireless, or the like. It shall be appreciated that the cellular communication device may be programmed to transmit data and/or notification signals either in a voice or data form depending upon patient preference or any other factor. Wireless transceiver 34 may also be a separate network communication device, such as 802.11, Bluetooth® or some other existing or later developed wireless communication protocol or technology.

In the illustrated embodiment, power supply 36 consists of one or more disposable and/or rechargeable batteries, which generally refers to an electrical energy storage device or storage system including multiple energy storage devices. A battery may include one or more separate electrochemical cells, each converting stored chemical energy into electrical energy by a chemical reaction to generate an electromotive force. Alkaline, nickel oxyhydroxide, lithium-copper, lithium-manganese, lithium-iron, lithium-carbon, lithium-thionyl chloride, mercury oxide, magnesium, zinc-air, zinc-chloride, or zinc-carbon battery are examples of disposable batteries insofar as they are generally not rechargeable and are discarded or recycled after discharge. Lead-acid batteries, valve regulated lead-acid batteries, sealed gel-cell batteries, and various "dry cell" batteries such as nickel-cadmium (NiCd), nickel-zinc (NiZn), nickel metal hydride (NiMH), and lithium-ion (Li-ion) are representative examples of the types of rechargeable batteries which may be utilized within power supply 36. In the event rechargeable batteries are used, charger 38 may be a direct connect charger have a connection to an external power supply or an inductive charger capable of wireless charging, such as that according to the Qi standard. Alternatively, in the event disposable batteries are used, the charger 38 may be omitted. In another form, charger 38 may be a kinetic charger or a solar charger. However, it is preferable that batteries, whether rechargeable or disposable, having sufficient capacity to power the dispensing all of the pills housed within pill storage 30 as well as the daily usage over an extended period, such as one month or 3 months, be selected so as to prevent the patient from being required to recharge the dispenser 10.

As shown in FIG. 1, portable secure pill dispenser 10 also includes a first dispenser 40 and a second dispenser 50. First dispenser 40 is an electromechanical device which selectively collects and dispenses single pills from pill storage 30 and deposits them into pill holding area 16 when it is activated. The dispensing of a single pill by first dispenser 40 occurs via a dispensing orifice 15 and at least pill paths 41 and 42. In one form, second dispenser 50 is also an electromechanical device which selectively collects and dispenses single pills from pill storage 30 and deposits them into pill holding area 16 when it is activated. In an alternate form, first dispenser 40 and/or second dispenser 50 may be mechanical, and not electrically powered, such as by using spring loading or magnetic force. The dispensing of a single pill by second dispenser 50 also occurs via a dispensing orifice 15 and at least pill paths 51 and 52. Second dispenser 50 serves as a failsafe so as to ensure that medication may be released in a controlled fashion to the patient even in the event of a malfunction or other unintended event. For example, to overcome a failure, jam or other error with respect to the first dispenser 40, the processing unit 32 may fail over to utilize the second dispenser 50 to complete the desired operation. Alternatively or additionally, the second dispenser 50 may also be activated via code or remote signal to permit an excess dose or other accommodation to the patient. In order to more accurately sense when such a malfunction occurs, and thus enable or trigger the activation of the second dispenser 50, dispenser 10 may also include a pill detector 60 which may be located between the output of the first dispenser 40 and the dispensing orifice 15. In another form, the pill detector 60 may be located in or proximate the pill holding area 16. Additionally, in one form, the pill detector serves to detect each and every dispensation of a pill from both of the first dispenser 40 and the second dispenser 50 and returns that information to the processing unit 32. In a further form, one or more components, such as processing unit 32 and power supply 36 may be redundantly duplicated with respect to second dispenser 50 in order to provide further redundancy.

As shown in FIG. 1, portable secure pill dispenser 10 also includes a temperature regulation device 62 which, when provided, is operable to modify the ambient temperature within one or more areas of dispenser 10, including pill storage 30. Depending upon the method of modification desire and the vulnerability of the medication contained therein, the temperature regulation device 62 may increase and/or decrease the temperature in order to protect the medicine contained therein. The temperature regulation device 62 may be fan, a self-contained air conditioner, a compressor, a heat pump, a liquid cooling system, an inductive heater or the like, any of which may be powered by power supply 36. Alternatively, the temperature regulation device 62 may be a material utilized in the construction of dispenser 10, such as the exterior housing 12 (or a portion thereof), which naturally regulates temperature, such as for example a synthetic yarn with a carbon nanotube coating that is activated by temperature and humidity, releasing heat in warm humid conditions and trapping heat when conditions are cool and dry, which may be used as a liner therein or the like. Additionally, alerts to the user, or to the remote server, can be issued when the temperature is too high or to low (either in general or for the medication currently contained therein). In another form, a portion of the exterior housing may change colors or a light illuminate in a certain color to indicate one or both of these extreme temperature conditions.

Shown in FIG. 2 is a plan view of a representative deployment of a portable secure pill dispenser 10 utilizing existing and additional infrastructure. As shown in FIG. 2, according to the illustrative embodiment, in operation portable secure pill dispenser 10 interfaces with one or more wireless networks, one or more remote servers and one or more global positioning satellites (GPS), all interconnected by at least the communication pathways shown.

More specifically, portable secure pill dispenser 10 connects to cellular network 70 via wireless transceiver 34. Cellular network 70 is a communications link or communications network where the final communications link to an originating sending node or final receiving node in the network is via a wireless link. The cellular network 70 is distributed over land areas ("cells"), each cell served by at least one fixed-location transceiver known as a cell site, base station, or generically, a "cell tower" such as cell tower 71. This base station provides the cell with the network coverage which can be used for transmission of voice, data and other types of communication. In a cellular network 70, each cell uses a different set of frequencies from neighboring cells, to avoid interference and provide guaranteed bandwidth within each cell. In a cellular network 70, switching from one cell frequency to a different cell frequency is done electronically without interruption as various mobile devices with transceivers configured to communicate with the network (i.e. the originating or final receiver nodes) move from cell to cell during an ongoing continuous communication, all generally without a base station operator or manual switching. This is called the "handover" or "handoff." Typically, a new channel is automatically selected for the mobile device on the new base station which will serve it as the mobile device moves around in the cell. The mobile unit then automatically switches from the current channel to the new channel and communication continues. The most common example of a cellular network 70 is a mobile phone (cell phone) network. Cellular network 70 may comprise a variety of communication networks, including without limitation the universal mobile telecommunications system (UTMS), global system for mobile communication (GSM), and a code division of multiple access (CDMA) network, or similar technology. Cellular phone network 70 utilizes a large array of cell towers, such as representative cell tower 71 to establish a wireless bi-directional transmission link between portable secure pill dispenser 10 and remote server 74, which may comprise a wireless data link, such as the Evolution-Data Optimized (EVDO), Enhanced Data rates for GSM Evolution (EDGE), 3G, 4G, LTE, WiMax, Narrowband Internet of Things (NB-IoT) or other wireless data connection. In some embodiments, the portable secure pill dispenser 10 may from time to time connect to a data network 72, such as a wireless data network, which may implement the 802.11 wireless standard. Data network 72 is preferably the Internet, which is a TCP/IP based global network; however, the patient of the term "Internet" herein shall be understood to refer to at least a portion of any interconnected electronic network which interchanges data by packet-switching or some other technology, which may be accessed via a wireless or wired connection using wireless transceiver 34 or some other connection which may be provided for by dispenser 10, such as a hard-wired docking station or the like.

Remote server 74, which may operate at one or more physical locations, is configured as a web server that hosts application business logic 75 for a prescription medication compliance engine. In addition, database server 76 is connected to remote server 74 and is configured as a database server 76 for storing patient, prescription, positional and compliance information, which is at least partially received from one or more portable secure pill dispensers 10 and processed by remote server 74.

Remote server 74 includes one or more processors or CPUs and one or more types of memory. Each processor may be comprised of one or more components configured as a single unit. When of a multi-component form, a processor may have one or more components located remotely relative to the others. One or more components of each processor may be of the electronic variety defining digital circuitry, analog circuitry, or both. In one embodiment, each processor is of a conventional, integrated circuit microprocessor arrangement, such as one or more OPTERON processors supplied by ADVANCED MICRO DEVICES Corporation of One AMD Place, Sunnyvale, Calif. 94088, USA. Each memory is one form of a computer-readable device. Each memory may include one or more types of solid-state electronic memory, magnetic memory, or optical memory, just to name a few. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a solid state disk (SSD); a magnetically encoded hard disc, floppy disc, tape, or cartridge media; or a combination of any of these memory types, or other types not included in the above list. Also, each memory may be volatile, nonvolatile, or a hybrid combination of volatile and nonvolatile varieties. Moreover, although not shown to preserve clarity, remote server 74 may be coupled to a display and/or may include an integrated display and include one or more operator input devices such as a keyboard, mouse, track ball, light pen, and/or microtelecommunicator, to name just a few representative examples.

With respect to database server 76, it may be located near or geographically apart from but connected via network, such as network 72 or the Internet, to remote server 74. The data stored by database server 76 is typically organized to model aspects of the real world in a way that supports processes obtaining information about the world from the data. Access to the data is generally provided by a "Database Management System" (DBMS) consisting of an individual computer software program or organized set of software programs that allow user to interact with one or more databases providing access to data stored in the database (although patient access restrictions may be put in place to limit access to some portion of the data). The DBMS provides various functions that allow entry, storage and retrieval of large quantities of information as well as ways to manage how that information is organized. A database is not generally portable across different DBMSs, but different DBMSs can interoperate by using standardized protocols and languages such as Structured Query Language (SQL), Open Database Connectivity (ODBC), Java Database Connectivity (JDBC), or Extensible Markup Language (XML) to allow a single application to work with more than one DBMS.

Databases and their corresponding database management systems are often classified according to a particular database model they support. Examples include a DBMS that relies on the "relational model" for storing data, usually referred to as Relational Database Management Systems (RDBMS). Such systems commonly use some variation of SQL to perform functions which include querying, formatting, administering, and updating an RDBMS. Other examples of database models include the "object" model, the "object-relational" model, the "file", "indexed file" or "flat-file" models, the "hierarchical" model, the "network" model, the "document" model, the "XML" model using some variation of XML, the "entity-attribute-value" model, and others. Examples of commercially available database management systems include PostgreSQL provided by the PostgreSQL Global Development Group; Microsoft SQL Server provided by the Microsoft Corporation of Redmond, Wash., USA; MySQL and various versions of the Oracle DBMS, often referred to as simply "Oracle" both separately offered by the Oracle Corporation of Redwood City, Calif., USA; the DBMS generally referred to as "SAP" provided by SAP SE of Walldorf, Germany; and the DB2 DBMS provided by the International Business Machines Corporation (IBM) of Armonk, N.Y., USA. The database and the DBMS software may also be referred to collectively as a "database". Similarly, the term "database" may also collectively refer to the database, the corresponding DBMS software, and a physical computer or collection of computers. Thus the term "database" may refer to the data, software for managing the data, and/or a physical computer that includes some or all of the data and/or the software for managing the data.

In addition to the above, portable secure pill dispenser 10 receives signals from to plurality of global positioning satellites (GPS) 78 via its on-board GPS receiver 38 in order to accurately determine its position in real time. In some forms, the dispenser 10 may utilize cellular network 70 to assist it in determining its locations, such as by assisted GPS. This determined position is made available to processing unit 32 for use in reporting the position of secure pill dispenser 10 when desired.

Shown in FIG. 3 is a perspective design view of the exterior housing 12 of a portable secure pill dispenser 10 according to one representative form. As shown, the dispenser 10 includes pill holding area 16 formed at the bottom and the user interface 14 is presented as a touch screen along a portion of the cylindrical ring. The remaining surface of the upper portion of the dispenser 10 is covered in a texturized material to enhance grip.

Shown in FIG. 4 is another perspective design view of the portable secure pill dispenser 10 according to the representative form shown in FIG. 3, but having the upper portion of exterior housing 12 and related components secured thereto hidden from view. In this view, two central tubes can be seem which collectively or individually form the pill storage area 20. In one form, each central tube may store medication for dispensation by the first dispenser 40 and second dispenser 50 respectively. In the illustrated form, this upper section is removed from the dispenser 10 in order to be reloaded, and each central tube includes a spring loaded line of pills, whether in single file, offset line, or two-by-two arrangement, or the like, biased toward the bottom, for dispensation.

Illustrated in FIG. 5 is one set of steps involved in the configuration and deployment of a portable secure pill dispenser 10, such as that shown in FIG. 1. The process begins at start point 500 with a patient being prescribed a medication (stage 502). The patient selects a pharmacy to fulfill the prescription, such as by bringing the prescription to the pharmacy's physical location or by having the prescription called in or otherwise electronically submitted (stage 504). Next, it is determined that the prescription should be filled using a portable secure pill dispenser 10 (stage 506). This decision may be made to ensure compliance with the prescribed dosing regimen, to prevent abuse or to comply with legal requirements or regulations. In one form, the prescribing physician or the selected pharmacists may elect, determine or otherwise require that the prescription be filled and provided to the patient using a portable secure pill dispenser 10. In another form, the prescribed medication or one or more characteristics of the patient, such as a history of prescription drug abuse or a criminal record, may dictate the portable secure pill dispenser 10 be utilized. A new (or used and sterilized) portable secure pill dispenser 10 is selected by the pharmacist or other authorized individual filling the prescription (stage 508). The selected secure pill dispenser 10 may already have a full battery or may requirement the fitment of one therein or the charging of a rechargeable battery (stage 510). The pharmacist or other authorized individual next fills the portable secure pill dispenser with the correct quantity of the prescribed medication (stage 512). The quantity may depend upon the dosage schedule prescribed as well as other rules and regulations, including whether a two week, one month, three month or some other period of medication is prescribed as well as the daily dosage frequency and quantity of pills required for each dose. Next, the pharmacist or other authorized individual, or someone or software designated by them, must program the portable secure pill dispenser 10 to the patient and prescription (stage 514). This may be accomplished using the user interface 14, the wireless transceiver 34 or a combination of the two. Alternatively, other programming means may be provided, such as a data connection or docking station. The programming of the portable secure pill dispenser 10 includes a unique identified (which may be linked in the HIPPA compliant database to the identity of the patient), the dosage regimen, and conditions/restrictions placed upon the dispenser's ability to dispense medication. Examples of such restrictions include no second dose dispensing following a prior dose being dispensed within a given time frame, such as 2 hours, 4 hours, 6 hours, 8 hours, 12 hours, 16 hours, 24 hours or the like. However, no time restriction is required, and the dispenser 10 may be set to dispense on demand. Other restrictions include no dispensing of medication within certain geo-fence defined "hot zones", which may be areas defined by local law enforcement as areas of widespread drug abuse. Other programming may include reminder frequency specifying how the portable secure pill dispenser 10 should issue reminders to the patient to comply with the dosing schedule and also tracking parameters, which specify how and when the dispenser 10 should report back to the remote server 74. For example, the dispenser 10 may report using the wireless transceiver 34 and infrastructure shown in FIG. 2 back to the remote server 74 periodic tracking information for the device, as determined by its GPS receiver, or only this information when a geo-fenced area is either broken or entered, or only when a dose is dispensed. All of this pre-set instructions and programming information are stored by the processing unit 32, such as in its transitory memory. Once this data is confirmed and verified, the patient is trained on how to use the portable secure pill dispenser 10 (stage 516). Subsequently, the patient is released with the secure pill dispenser 10 for use (stage 518). The process ends, or proceeds to the process shown in FIG. 6, at end point 520.

Illustrated in FIG. 6 is one set of steps which may occur during exemplary operation of the portable secure pill dispenser 10 shown in FIG. 1. The process begins at start point 600 with the patient taking possession of the dispenser after having been freshly loaded with the patient's prescribed medication (stage 602). The wireless transceiver 34 begins communicating with remote server 74 to initialize (stage 604). The remote server 74 knows which patient has custody (or responsibility for) the reporting dispenser as its unique ID or other identifying information is associated with the patient in database 76 as a result of the provisioning process described in FIG. 5. In the illustrated form, from this point forward the dispenser only reports to the remote server 74 upon the occurrence of one of a plurality of predefined events. This set of predefined events may include the dispensing of a pill, the requested dispensing of a pill that was denied, an attempt to tamper with the dispenser, the entry of a dispenser within a restricted area, the departure of the dispenser 10 from within a confined area, the occurrence of any error, and the like. For example, the next event which occurs is the patient requesting the dispensation of one or more pills (stage 606). This may occur via the patient interacting with the user interface 14, and the input is passed along to the processing unit 32. Moreover, the number of pills to be dispensed may be preset into the dispenser 10 according to the prescription. In response, provided no restrictions are in place within dispenser 10, such as time from last dispensation, the dispenser 10 attempts to dispense the pill or pills into the pill holding area 16 by activating the first dispenser 40 (stage 608). In the case of multiple pills in a dose, the first dispenser 40 may be serially activated a number of times by the processing unit 32. After each activation of the first dispenser 40, the pill detector 60 determines whether or not a pill was actually dispensed into the pill holding area 16 (stage 610). In the event the pill is detected, the process proceeds as normal. However, in the event the pill was not detected (stage 612), then the processing unit 32 may attempt to activate first dispenser 40 one or more times until successful (stage 614). Ultimately, if unable to verify the dispensation of a pill using pill detector 60, the processing unit 32 may fail over and attempt to dispense a pill using second dispenser 50 (stage 616). After activation of the second dispenser 50, pill detector 60 again seeks to verify the proper dispensation and is able to do so (stage 618). The process next proceeds to the occurrence of a predetermined event, in this case, the attempt by the patient to dispense a second pill immediately following a first dispensation (stage 620). The dispenser 10 and processing unit 32 reports this event to remote server 74 using wireless transceiver 34 (stage 622). Upon receipt, the remote server 74 stores data regarding the event in association with the patient in database 76 and may also take any actions programmed therein, such as to automatically notify the proper authorities or the prescribing physician or attending pharmacist (stage 624). The process concludes with the patient presumably completing the course of the medication and returning the dispenser 10 the appropriate issuing entity as instructed (stage 626) and ends at end point 628.

In an alternate form, the second dispenser 50 may only be activated by the entry of a code or other authorization into the user interface 14 or processing unit 32 by the patient, or via an authorization received from the remote server 74 received via wireless transceiver 34. This arrangement provides a fail safe to the dispenser 10 and in particular first dispenser 40. To further enhance this effect, the second dispenser and any needed components to effect its operation may be supported by a back-up battery separate from the power supply 36. Alternatively or additionally, the second dispenser 50 may have a separate repository of one or more pills, distinct from pill storage 30, so as to dispense one or more doses in an emergency before the patient can obtain a replacement dispenser 10. The novel aspect of a fail-safe contained the present invention is essential to any pill dispenser which seeks to provide access control for abused medications and/or controlled substances, which inherently requires restricting access, but also must provide some form of backup as the inability of the patient to obtain their medication from the dispenser may also present significant healthcare issues, including the potential for serious complications, including death.

In a further form, pill detector 60 may include one or more pill detectors on the same or related type, so as to ensure the protect detection of pill dispensation and to prevent the unintended over dispensation of pills.

In alternate forms, the dispenser 10 may report information to remote server 74 more often than upon the infrequent occurrence of one of the predefined events, such as periodically every hour or the like, provided the battery resources are sufficient.

In a further form, the patient may utilize a smartphone, computer or the like to attempt to locate the dispenser 10 in the event it is lost or misplaced. To do so, a request is transmitted to the remote server 74 which then issues a command to the dispenser 10, which is received via wireless transceiver 34. The dispenser 10 may report back its GPS location, as determined by GPS receiver 38, which may then be passed along to the patient, such as for display on their smartphone or computer to assist in locating the dispenser 10. Alternatively or additionally, the request sent to the dispenser 10 may also cause the dispenser 10 to play an audible sound or flash some exterior lights in order to aid the patient in locating the dispenser 10.

Shown in FIG. 7 is one set of steps for use in the process of receiving a return of a portable secure pill dispenser 10 and reconditioning it for subsequent use. It shall be appreciated that while a portable secure pill dispenser 10 of the present invention may be disposable, re-use is preferred. The process begins at start point 700 with the used portable secure pill dispenser 10 being received back from the patient (stage 702). The patient to which the dispenser 10 was previously assigned is identified and disassociated in the remote server 74 (stage 704). The dispenser 10 may be returned when a prescription refill is sought, at the end of a prescription course, or through some other means, such as by mail our courier to the pharmacy or distributor/manufacturer/service provider of the dispenser 10. Upon receipt, the remaining medicine within the dispenser 10 is logged and stored in association with the patient and prescription within database 76 by remote server 74 (stage 706). All remaining medication and the medication is disposed of in a responsible way approved by the appropriate agencies (stage 708). Next, the dispenser 10, or at least a portion thereof, is put through a sanitization process, which may involve the use of various chemicals, heat, steam or the like, but which is designed to sterilize the dispenser 10 for reuse. In one form, the sanitization process takes place in accordance guidelines and procedures set forth by the National Institute of Health, such as Annex I: Cleaning and disinfection of respiratory equipment (available at http://www.ncbi.nlm.nih.gov/books/NBK214361), the content of which is hereby incorporated by reference. The dispenser 10 will then be tested to ensure its proper operation (stage 710). The dispenser 10 will also, either before or after testing, be recharged (or fitted with a replacement battery), depending on the type of battery utilized (stage 712). Lastly, the dispenser 10 is repackaged and redeployed to a distributor, pharmacy or other authorized user for subsequent redeployment and reuse (stage 714). The proceed ends at end point 716.

While the invention has been illustrated and described in detail in the drawings and foregoing description, the same is to be considered as illustrative and not restrictive in character, it being understood that only the preferred embodiment has been shown and described and that all equivalents, changes, and modifications that come within the spirit of the inventions as described herein and/or by the following claims are desired to be protected. Hence, the proper scope of the present invention should be determined only by the broadest interpretation of the appended claims so as to encompass all such modifications as well as all relationships equivalent to those illustrated in the drawings and described in the specification.

What is claimed is:
1. A portable pill dispenser comprising:
an exterior housing;
a first container within the exterior housing defining an interior that can accommodate a plurality pills;
a dispensing orifice of sufficient size to allow at least one of said plurality of pills to pass through;
a power source including at least one battery;
a first dispenser, powered by the power source, operable to collect a first single pill from the interior of said first container and dispense the first single pill through the dispensing orifice and out of the interior;
a second dispenser, independent from said first dispenser, operable to dispense a second single pill from the first container, wherein the first and second dispensers are independent and separately operable of one other;
a processing unit secured to the first container, powered by the power source, and electronically connected to at least the first dispenser, wherein the processing unit is operable to selectively activate the first dispenser to dispense a first predetermined quantity of pills; and
an electronic user interface operable to provide patient input to the processing unit.

2. The portable pill dispenser of claim 1, wherein the second dispenser is operable to dispense the second single pill through the dispensing orifice.

3. The portable pill dispenser of claim 1, wherein the second dispenser is further operable to collect the second single pill from the interior of said first container.

4. The portable pill dispenser of claim 1, further comprising:
a pill detector connected to the dispensing orifice and communicatively coupled to the processing unit, the pill detector configured to detect the act of dispensing a first single pill through the dispensing orifice, and in response provide a first signal to the processing unit.

5. The portable pill dispenser of claim 1, further comprising:
a pill track located within the interior for securely storing the plurality of pills in an ordered fashion; wherein the pill track terminates at the first dispenser.

6. The portable pill dispenser of claim 5, wherein the pill track is spring or magnetically driven so as to urge pills contained in the pill track toward the first dispenser.

7. The portable pill dispenser of claim 1, wherein the first predetermined quantity of pills is greater than one.

8. The portable pill dispenser of claim 1, further comprising:
  a tamper sensor communicatively coupled to the processing unit, the tamper sensor configured to detect the unauthorized act of breaking into the interior and in response provide a second signal to the processing unit.

9. The portable pill dispenser of claim 1, further comprising:
  a pill holding area formed in the exterior housing which is fed by the dispensing orifice.

10. The portable pill dispenser of claim 9, further comprising:
  a locking mechanism, connected to and controlled by the processing unit, which selectively provides access to the pill holding area.

11. The portable pill dispenser of claim 1, further comprising:
  a wireless transceiver, powered by the power source, and connected to the processing unit.

12. The portable pill dispenser of claim 11, wherein the wireless transceiver is operable to transmit data to a remote server following the occurrence of each activation of the first dispenser.

13. The portable pill dispenser of claim 11, further comprising:
  a global positioning system (GPS) sensor;
    wherein the wireless transceiver is further operable to automatically transmit position data from the GPS sensor to a remote server upon the occurrence of a predefined event.

14. The portable pill dispenser of claim 1, wherein the processing unit is operable to selectively activate the second dispenser to dispense a second predetermined quantity of pills only after receiving from the wireless transceiver an authorization from a remove server.

15. The portable pill dispenser of claim 1, wherein the authorization includes an access code.

16. The portable pill dispenser of claim 1, further comprising:
  a combination lock, having a second user interface for accepting the entry of a combination, wherein the combination lock controls the operation of the second dispenser.

17. The portable pill dispenser of claim 1, wherein the processing unit prevents the operation of the second dispenser unless the first dispenser is in a state of error.

18. The portable pill dispenser of claim 13, wherein the predetermined event is the activation of the second dispenser.

19. The portable pill dispenser of claim 13, further comprising:
  a temperature regulator, powered by the power source and controlled by the processing unit, which selectively alters the temperature of the interior toward a predetermine temperature.

20. The portable pill dispenser of claim 1, further comprising:
  a wireless charging receiver operable to receive power from an external wireless power transmitter to charge the at least one battery.

* * * * *

UNITED STATES PATENT AND TRADEMARK OFFICE
CERTIFICATE OF CORRECTION

PATENT NO. : 11,213,457 B2  
APPLICATION NO. : 16/865947  
DATED : January 4, 2022  
INVENTOR(S) : Anthony John Guarascio and Richard Michael Ribellino, Jr.

Page 1 of 1

It is certified that error appears in the above-identified patent and that said Letters Patent is hereby corrected as shown below:

In the Claims

Column 14, Claim 14, Line 5, replace "remove" with --remote--

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*